United States Patent [19]
Diouf et al.

[11] Patent Number: 5,387,586
[45] Date of Patent: Feb. 7, 1995

[54] (ARYL(ALKYL)CARBONYL)-HETEROCYCLIC COMPOUNDS, COMPOSITIONS AND USE

[75] Inventors: Ousmane Diouf, Villeneuve d'Ascq; Daniel Lesieur, Gondecourt; Patrick Depreux, Armentieres; Béatrice Guardiola-Lemaitre, Saint-Cloud; Daniel-Henri Caignard, Paris; Pierre Renard, Versailles; Gérard Adam, Le Mesnil le Roi, all of France

[73] Assignee: Adir et Compagnie, Courbevoie, France

[21] Appl. No.: 206,451

[22] Filed: Mar. 4, 1994

[30] Foreign Application Priority Data

Mar. 5, 1993 [FR] France ............... 93 02528

[51] Int. Cl.$^6$ ............ A61K 31/445; A61K 31/535; C07D 417/06; C07D 417/14
[52] U.S. Cl. ........................ 514/233.8; 514/321; 544/130; 544/364; 544/368; 546/198
[58] Field of Search ........... 544/130, 364, 368; 546/198; 514/233.8, 321

[56] References Cited

U.S. PATENT DOCUMENTS 4,035,369  7/1977  Vandenberk ............... 546/198

OTHER PUBLICATIONS

Shoji et al., *Chemical Abstracts*, vol. 112 (1990) No. 98389n.
Sugimoto et al., *Chemical Abstracts*, vol. 106 (1987) No. 213,767z.

*Primary Examiner*—Robert W. Ramsuer
*Attorney, Agent, or Firm*—Gordon W. Hueschen

[57] ABSTRACT

The invention relates to a compound selected from those of formula (I):

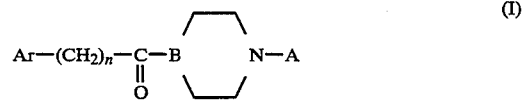

wherein Ar, n, B and A are as defined in the description, to their optical isomers, and to their addition salts thereof with a pharmaceutically-acceptable acid or base.

Medicinal product which is useful for treating pain and treating or preventing pathologies which require psychotropic agents.

9 Claims, No Drawings

(ARYL(ALKYL)CARBONYL)-HETEROCYCLIC COMPOUNDS, COMPOSITIONS AND USE

The present invention relates to new (aryl(alkyl)carbonyl)-heterocyclic compounds, to processes for preparing them and to pharmaceutical compositions containing them.

It is known that 5-HT$_2$ serotoninergic receptors are associated with an improvement in schizophrenic conditions. They have also shown beneficial effects in anxiety and depression.

Compounds having a good affinity for these 5-HT$_2$ receptors would therefore be useful in the clinical situation for the treatment of these pathologies.

The Applicant has discovered new (aryl(alkyl)carbonyl)-heterocyclic compounds which have a high affinity for 5-HT$_2$ receptors, some of these compounds also surprisingly having an analgesic activity.

Heterocyclic compounds, described as having an affinity for melatoninergic receptors, are known from the state of the art (Patent Application EP 506539) but these compounds do not have any comparable affinity for 5-HT$_2$ receptors nor do they have any analgesic activity.

More particularly, the invention relates to the compounds of formula (I):

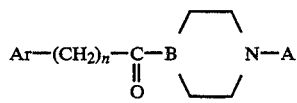

in which:

Ar: represents a phenyl or naphthyl group, Ar being unsubstituted or substituted by one or more radicals chosen from halogen, lower alkyl, lower alkoxy and trifluoromethyl, n: represents 0 or an integer from 1 to 4, B: represents a

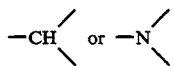

group, and,

A: represents a group of formula (A1) or (A2):

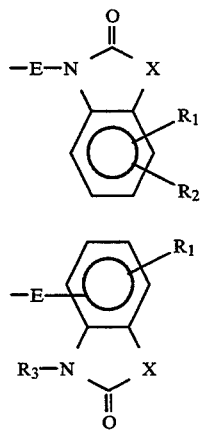

in which

E: represents a linear or branched alkylene chain containing 1 to 6 carbon atoms, R$_1$: represents a radical chosen from hydrogen, hydroxyl, lower alkyl and lower alkoxy, R$_2$: represents a radical chosen from hydrogen, lower alkyl and

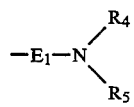

where E$_1$ has the same definition as E as described above and where R$_4$ and R$_5$ are chosen, independently from one another, from hydrogen and lower alkyl, or form, together with the nitrogen atom which carries them, a heterocycle chosen from pyrrolidine, piperidine, substituted piperidine, morpholine, piperazine and substituted piperazine, R$_3$: represents a radical chosen from hydrogen and lower alkyl, and X: represents a sulfur or oxygen atom, to their optical isomers, and to their addition salts with a pharmaceutically acceptable base or acid, it being understood that, except when otherwise specified, the terms "lower alkyl" and "lower alkoxy" denote linear or branched groups containing 1 to 6 carbon atoms, and the term "substituted" assumed by the "piperidine" and "piperazine" heterocycles means that these heterocycles can be substituted in the 4-position by a radical chosen from lower alkyl, aryl and lower arylalkyl, the term "aryl" denoting a phenyl, naphthyl or pyridyl group which can itself be unsubstituted or substituted by one or more radicals chosen from halogen, lower alkyl, hydroxyl, lower alkoxy and trifluoromethyl.

Mention may be made, among pharmaceutically acceptable acids which can be used to form an addition salt with the compounds of the invention, by way of examples and in a non-limiting way, of hydrochloric, sulfuric, phosphoric, tartaric, malic, maleic, fumaric, oxalic, methanesulfonic, ethanesulfonic, camphoric and citric acids.

Mention may be made, among pharmaceutically acceptable bases which can be used to salify the compounds used according to the invention, by way of examples and in a non-limiting way, of sodium hydroxide, potassium hydroxide, triethylamine, diethylamine, ethanolamine, arginine, lysine and diethanolamine.

The invention applies to the process for the preparation of the compounds of formula (I), wherein a compound of formula (II):

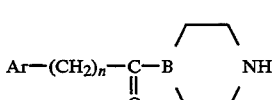

in which Ar, n and B are as defined in the formula (I), is reacted with a compound of formula (III/A1):

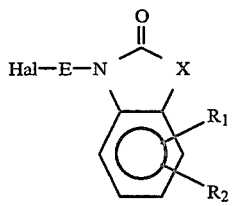

(III/A1)

or of formula (III/A2):

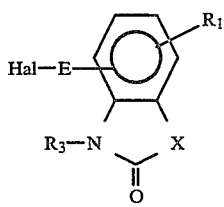

(III/A2)

in which E, X, R$_1$, R$_2$ and R$_3$ are as defined in the formula (I) and Hal represents a halogen atom, in order to obtain the corresponding compound of formula (I), the compounds of formula (I) being, if appropriate:
  purified according to one or more purification methods chosen from crystallization, chromatography on a silica column, extraction, filtration and passing through charcoal or resin,
  separated, in the pure form or in the form of mixtures, into their optical isomers,
  and salified with a pharmaceutically acceptable acid or base.

The invention also applies to the process for obtaining compounds of formula (I/a):

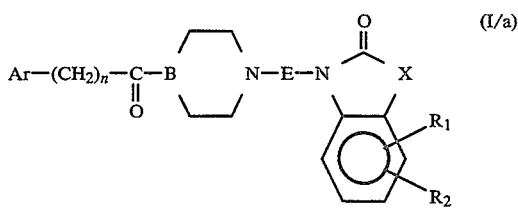

(I/a)

in which Ar, n, B, E, X, R$_1$ and R$_2$ are as defined in the formula (I), wherein a compound of formula (IV):

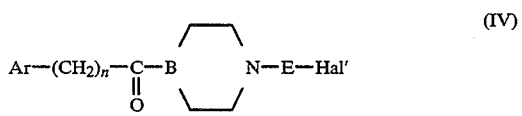

(IV)

in which Ar, n, B and E are as defined above and Hal' represents a halogen atom, is reacted with a compound of formula (V):

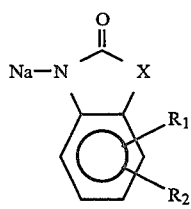

(V)

in which X, R$_1$ and R$_2$ are as described above, in order to obtain the corresponding compounds of formula (I/a), the compounds of formula (I/a) being, if appropriate:
  purified according to one or more purification methods chosen from crystallization, chromatography on a silica column, extraction, filtration, and passing through charcoal or resin,
  separated, in the pure form or in the form of mixtures, into their optical isomers,
  and salified with a pharmaceutically acceptable acid or base.

The starting materials used in the processes described above are either commercially available or easily accessible to those skilled in the art according to processes known from the literature or proposed during the preparation examples described below.

The compounds of formula (II) are, for example, easily accessible to those skilled in the art by reacting a compound of formula (II/a):

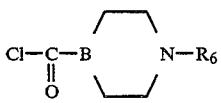

(II/a)

in which B is as described in formula (I) and R$_6$ represents a hydrogen atom or a protecting group of the nitrogen, with a compound of formula (II/b):

Ar (II/b)

in which Ar is as defined in the formula (I), or with a compound of formula (II/c):

Ar—(CH$_2$)$_n$—MgBr (II/c)

in which Ar and n are as defined in the formula (I), in order to obtain, if appropriate after removal of the protecting group R$_6$, the corresponding compounds of formula (II).

The compounds of formula (IV) are also easily obtained by reacting a compound of formula (II):

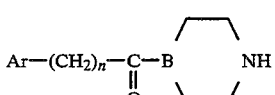

(II)

in which Ar, n and B are as defined in the formula (I), with an alcohol of formula (VI):

Hal'—E—OH (VI)

in which E is as defined in the formula (I) and Hal' represents a halogen atom, in order to obtain the corresponding compound of formula (IV).

The compounds of formula (III/A1) and (III/A2) are easily accessible to those skilled in the art according to processes analogous to those described in Application EP 506539.

The Applicant has discovered that the compounds of the invention had a remarkable affinity for 5-HT$_2$ serotoninergic receptors.

This very significant binding ability is revealed in Example A of the present document (Example A: Measurement of the affinity for serotoninergic receptors).

This high affinity for 5-HT$_2$ receptors shown by the compounds of the invention turns out to be surprising since the compounds of the prior art mentioned in Application EP 506539 do not in the least show such an affinity for these receptors.

The antipsychotic activity of the compounds of the invention was shown by the test of antagonism of amphetamine-induced hyperactivity (Example B of the present application: Study of antagonism of amphetamine-induced hyperactivity).

The compounds of the invention also have an anxiolytic activity (Example C: Light-dark cage test).

The equally surprising analgesic activity of the compounds of the invention is shown in Example D (hotplate test).

The compounds of the invention, by their method of action, are therefore new candidates for the treatment and prevention of pathologies which require psychotropic agents, and the treatment of conditions involving pain.

The compounds of the invention are more particularly useful in the treatment and prevention of anxiety, depression and depressive syndromes, psychotic conditions and Parkinson's disease and the treatment of pain.

Another subject of the present invention is pharmaceutical compositions containing, as active principle, one or more compounds of formula (I), or their addition salts with a pharmaceutically acceptable acid or base, in combination with one or more pharmaceutically acceptable excipients, vehicles or diluents.

Mention can be made, among pharmaceutical compositions according to the invention, by way of examples and in a non-limiting way, of those which are suitable for oral, parental, nasal, rectal, perlingual, ocular or pulmonary administration and especially injectable preparations, aerosols, eye- or nosedrops, simple, film-coated or sugar-coated tablets, capsules, including gelatin capsules, suppositories, creams, ointments and dermal gels.

The useful dose varies according to the age and weight of the patient, the administration route, the nature of the ailment and possible associated treatments and ranges between 0.05 mg and 50 mg per 24 hours taken once or twice.

EXAMPLE 1

3-{2-[4-(4-Fluorobenzoyl)piperidino]ethyl}benzothiazolin-2-one

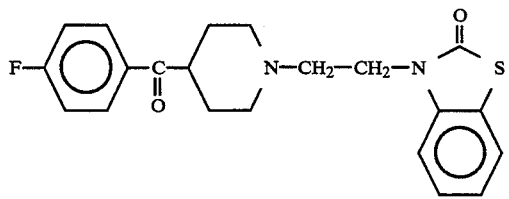

STAGE A 1-(2-Chloroethyl)-4-(4-fluorobenzoyl)piperidine 1-acetylpiperidine-4-carboxylic acid 1-Acetylpiperidine-4-carboxylic acid is prepared by bringing a solution of piperidine-4-carboxylic acid in acetic anhydride to reflux for 2 hours and then stirring for 16 hours at room temperature. The solution is then concentrated and the residue is triturated in ether. The solid compound is recovered by filtration.

Recrystallization solvent: isopropanol/isopropyl ether

Melting point: 180°–182° C.

1-acetyl-4-(4-fluorobenzoyl)piperidine

1-Acetylpiperidine-4-carboxylic acid is poured into a thionyl chloride solution. The acyl chloride formed precipitates from solution. The solid is dried after washing several times with petroleum ether. The infrared spectrum shows complete conversion of the acid to the acyl chloride. The acyl chloride is slowly added to aluminum chloride in solution in fluorobenzene, with stirring. The mixture is then brought to reflux for 1 hour. The mixture is poured onto ice and the two resulting phases are separated. The aqueous phase is extracted twice with chloroform and the extracts are added to the fluorobenzene separated previously. The organic solution is dried ($Na_2SO_4$) and filtered. The filtrate is concentrated under reduced pressure and a crystalline white solid is obtained.

Melting point: 75°–78° C.

4-(4-fluorobenzoyl)piperidine

A solution of 1-acetyl-4-(4-fluorobenzoyl)piperidine in 6N hydrochloric acid is brought to reflux for 2 hours. The solution is cooled and then extracted twice with ether. The aqueous solution is made basic (NaOH) and then extracted with benzene. The extracts are dried ($Na_2SO_4$) and filtered. The filtrate is concentrated under reduced pressure and the residual oil is converted to a hydrochloric acid salt.

Melting point (hydrochloride): 222°–224° C.

1-(2-chloroethyl)-4-(4-fluorobenzoyl)piperidine 0.01 mol of the hydrochloride of 4-(4-fluorobenzoyl)piperidine in an ethanolic sodium hydroxide solution is introduced into a 250 cm³ round-bottomed flask equipped with a water-cooled reflux condenser. The reaction mixture is brought to reflux and 0.012 mol of 2-bromoethanol is added. Reflux is maintained for 2 hours, the mixture is allowed to cool, the inorganic precipitate formed is filtered off and the alcohol is evaporated under reduced pressure.

The residue is taken up in 75 cm³ of anhydrous chloroform, the mixture is cooled in an ice bath, 0.04 mol of thionyl chloride is added, a water-cooled reflux condenser is fitted and the reaction is continued for four hours at reflux of the solvent. The mixture is allowed to cool, the chloroform is evaporated and then the residue is taken up in absolute alcohol and brought to boiling point in order to remove the thionyl chloride.

The absolute alcohol is evaporated and an anhydrous acetone solution saturated with gaseous hydrochloric acid is added to the residue. The precipitate obtained is filtered off and then recrystallized.

Melting point (hydrochloride): 110°–112° C.

Yield: 65%

Recrystallization solvent: anhydrous acetone

Elemental analysis: Calculated: C % 52.27 H % 6.14 N % 4.38 Found: C % 52.68 H % 6.18 N % 4.41 Infrared spectrometry: 3000–2600 cm$^{-1}$ ν CH (alkyls) 1670 cm$^{-1}$ ν CO 1610–1580 cm$^{-1}$ ν C═C (aromatics)

STAGE B:

3-{2-[4-(4-Fluorobenzoyl)piperidino]ethyl}benzothiazolin-2-one 0.01 mol of benzothiazolin-2-one is dissolved in dimethylformamide in a 250 cm³ ground-neck flask equipped with a water-cooled reflux condenser. 0.06 mol of potassium carbonate is added and the mixture is brought to reflux. The mixture is left stirring for 30 minutes and 0.012 mol of the hydrochloride of 1-(2-chloroethyl)-4-(4-fluorobenzoyl)piperidine, dissolved beforehand in dimethylformamide, is added. Stirring is continued for one hour, the mixture is allowed to cool, the inorganic insoluble material is filtered off and the filtrate is poured onto crushed ice.

The precipitate obtained is filtered off, dried, dissolved in anhydrous acetone and then the hydrochloride is precipitated by sparging with a stream of dry gaseous hydrochloric acid. The product obtained is filtered off, dried and then recrystallized.

Melting point (hydrochloride): 25°–256° C.
Yield: 67%

Recrystallization solvent: absolute alcohol

Basic nitrogen assay: for three basic nitrogens Basic nitrogen percentage, theory: 5.67% Basic nitrogen percentage, found: 5.86%

Elemental analysis: (title compound + 3$H_2O$) Calculated: C % 51.60 H % 5.15 N % 6.97 Found: C % 51.93 H % 5.37 N % 6.73 Infrared spectrometry: 3100–2800 $cm^{-1}$ v CH (alkyls) 2700–2300 $cm^{-1}$ v $NH^+$ 1670 $cm^{-1}$ v CO (NCOS+ketone) 1590 $cm^{-1}$ v C=C (aromatics) 1020 $cm^{-1}$ v $OCH_3$

EXAMPLE 4

3-{2-[4-(4-Fluorobenzoyl)piperidino]ethyl}-6-(4-morpholinobutyl)benzothiazolin-2-one

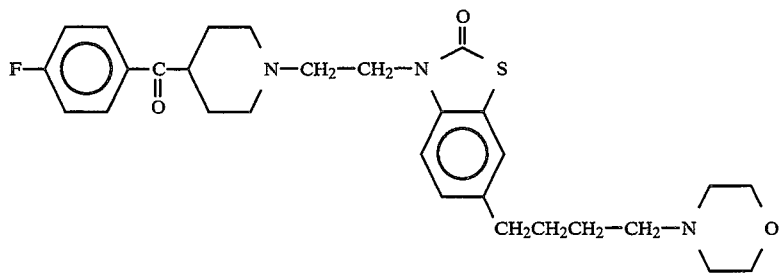

Recrystallization solvent: anhydrous acetone

Basic nitrogen assay: for one basic nitrogen Basic nitrogen percentage, theory: 3.33% Basic nitrogen percentage, found: 3.61%

Elemental analysis: (title compound + 7/2 $H_2O$) Calculated: C % 52.18 H % 5.16 N % 5.95 Found: C % 52.11 H % 5.55 N % 5.78 Infrared spectrometry: 3100–2800 $cm^{-1}$ v CH (alkyls) 2700–2300 $cm^{-1}$ v $NH^+$ 1610 $cm^{-1}$ v CO (NCOS+ketones) 1580 $cm^{-1}$ v C=C

EXAMPLE 2

3-{2-[4-(4-Fluorobenzoyl)piperidino]ethyl}-6-{4-[4-(3-trifluoromethylphenyl)piperazinyl]butyl}benzothiazolin-2-one The title compound is obtained by carrying out the reaction as in Example 1 but replacing benzothiazolin-2-one with the dihydrochloride of 6-{4-[4-(3-trifluoromethylphenyl)piperazinyl]butyl}benzothiazolin-2-one.

Melting point (trihydrochloride): 250°–252° C.
Yield: 37%

Recrystallization solvent: absolute alcohol

Basic nitrogen assay: for three basic nitrogens Basic nitrogen percentage, theory: 5.39% Basic nitrogen percentage, found: 5.31%

Infrared spectrometry: 3080–2840 $cm^{-1}$ v CH (alkyls) 2500–2000 $cm^{-1}$ v $NH^+$ 1670 $cm^{-1}$ v CO (NCOS+ketones) 1580 $cm^{-1}$ v C=C (aromatics)

EXAMPLE 3

3-{2-[4-(4-Fluorobenzoyl)piperidino]ethyl}-6-{4-[4-(2-methoxy-phenyl)piperazinyl]butyl}benzothiazolin-2-one The title compound is obtained by carrying out the reaction as in Example 1 but replacing benzothiazolin-2-one with the dihydrochloride of 6-{4-[4-(2-methoxyphenyl)piperazinyl]butyl}benzothiazolin-2-one.

Melting point (trihydrochloride): 252°–254° C.
Yield: 30%

The title compound is obtained by carrying out the reaction as in Example 1 but replacing benzothiazolin-2-one with the dihydrochloride of 6-(4-morpholinobutyl)benzothiazolin-2-one.

Melting point (dihydrochloride): 258°–260° C.

EXAMPLES 5 TO 22

By carrying out the reaction as in Example 1 but replacing benzothiazolin-2-one in Stage B with:
6-(2-morpholinoethyl)benzothiazolin-2-one, there is obtained:

EXAMPLE 5

3-{2-[4-(4-Fluorobenzoyl)piperidino]ethyl}-6-(2-morpholinoethyl)benzothiazolin-2-one 6-[2-(4-phenylpiperazinyl)ethyl]benzothiazolin-2-one, there is obtained:

EXAMPLE 6

3-{2-[4-(4-Fluorobenzoyl)piperidino]ethyl}-6-[2-(4-phenylpiperazinyl)ethyl]benzothiazolin-2-one 6-{2-[4-(3-trifluoromethylphenyl)piperazinyl]ethyl]benzothiazolin-2-one, there is obtained:

EXAMPLE 7

3-{2-[4-(4-Fluorobenzoyl)piperidino]ethyl}-6-{2-[4-(3-trifluoromethylphenyl)piperazinyl]ethyl}benzothiazolin-2-one 6-(N,N-dipropylaminoethyl)benzothiazolin-2-one, there is obtained:

EXAMPLE 8

3-{2-[4-(4-Fluorobenzoyl)piperidino]ethyl}-6-(N,N-dipropylaminoethyl)benzothiazolin-2-one 6-{2-[4-(2,3,4-trimethoxyphenylmethyl)piperazinyl]ethyl}benzothiazolin-2-one, there is obtained:

EXAMPLE 9

3-{2-[4-(4-Fluorobenzoyl)piperidino]ethyl}-6-{2-[4-(2,3,4-trimethoxy phenylmethyl)piperazinyl]ethyl}benzothiazolin-2-one 6-methoxybenzothiazolin-2-one, there is obtained:

EXAMPLE 10

3-{2-[4-(4-Fluorobenzoyl)piperidino]ethyl}-6-methoxybenzothiazolin-2-one 6-hydroxybenzothiazolin-2-one, there is obtained:

EXAMPLE 11

3-{2-[4-(4-Fluorobenzoyl)piperidino]ethyl)-6-hydroxybenzothiazolin-2-one 5-methoxybenzothiazolin-2-one, there is obtained:

EXAMPLE 12

3-{2-[4-(4-Fluorobenzoyl)piperidino]ethyl}-5-methoxybenzothiazolin-2-one

Melting point: 248°–250° C.

6-(N,N-dipropylaminoethyl)-5-methoxybenzothiazolin-2-one, there is obtained:

EXAMPLE 13

3-{2-[4-(4-Fluorobenzoyl)piperidino]ethyl}-6-(N,N-dipropylaminoethyl)-5-methoxybenzothiazolin-2-one 6-{2-[4-(3-pyridyl)piperazinyl]ethyl}benzothiazolin-2-one, there is obtained:

EXAMPLE 14

3-{2-[4-(4-Fluorobenzoyl)piperidino]ethyl}-6-{2-[4-(3-pyridyl)piperazinyl]ethyl}benzothiazolin-2-one 6-{4-[4-(2-methylphenyl)piperazinyl]butyl}benzothiazolin-2-one, there is obtained:

EXAMPLE 15

3-{2-[4-(4-Fluorobenzoyl)piperidino]ethyl}-6-{4-[4-(2-methylphenyl)piperazinyl]butyl}benzothiazolin-2-one 5-methoxy-6-(4-morpholinobutyl)benzothiazolin-2-one, there is obtained:

EXAMPLE 16

3-{2-[4-(4-Fluorobenzoyl)piperidino]ethyl}-5-methoxy-6-(4-morpholinobutyl)benzothiazolin-2-one 6-[4-(4-naphthylpiperazinyl)butyl]benzothiazolin-2-one, there is obtained:

EXAMPLE 17

3-{2-[4-(4-Fluorobenzoyl)piperidino]ethyl}-6-[4-(4-napththylpiperazinyl)butyl]benzothiazolin-2-one 6-{4-[4-(4-methoxynaphthyl)piperazinyl]butyl}benzothiazolin-2-one, there is obtained:

EXAMPLE 18

3-{2-[4-(4-Fluorobenzoyl)piperidino]ethyl}-6-{4-[4-(4-methoxynaphthyl)piperazinyl]butyl}benzothiazolin-2-one 6-{2-[4-(2-methoxyphenyl)piperazinyl]ethyl}benzothiazolin-2-one, there is obtained:

EXAMPLE 19

3-{2-[4-(4-Fluorobenzoyl)piperidino]ethyl}-6-{2-[4-(2-methoxyphenyl)piperazinyl]ethyl}benzothiazolin-2-one 6-[2-(4-phenylpiperidino)ethyl]benzothiazolin-2-one, there is obtained:

EXAMPLE 20

3-{2-[4-(4-Fluorobenzoyl)piperidino]ethyl}-6-[2-(4-phenylpiperidino)ethyl]benzothiazolin-2 -one 6-[3-(4-phenylpiperazin-1-yl)propyl]benzothiazolin-2-one, there is obtained:

EXAMPLE 21

3-{2-[4-(Fluorobenzoyl)piperidino]ethyl}-6-[3-(4-phenylpiperazinyl)propyl]benzothiazolin-2-one 6-[4-(4-phenylpiperazin-1-yl)butyl]benzothiazolin-2-one, there is obtained:

EXAMPLE 22

3-{2-[4-(4-Fluorobenzoyl)piperidino]ethyl}-6-[4-(4-phenylpiperazinyl)butyl]benzothiazolin-2-one

EXAMPLE 23

3-{2-[4-(3,4-Dimethoxybenzoyl)piperidino]ethyl}benzothiazolin-2-one

The title compound is obtained by carrying out the reaction as in Example 1 but starting from 4-(3,4-dimethoxybenzoyl)piperidine in place of 4-(4-fluorobenzoyl)piperidine.

EXAMPLE 24

3-{2-[4-(4-Methoxybenzoyl)piperidino]ethyl}benzothiazolin-2-one

The title compound is obtained by carrying out the reaction as in Example 1 but starting from 4-(4-methoxybenzoyl)piperidine in place of 4-(4-fluorobenzoyl)piperidine.

EXAMPLE 25

3-[2-(4-Benzoylpiperidino)ethyl]benzothiazolin-2-one

The title compound is obtained by carrying out the reaction as in Example 1 but starting from 4-benzoylpiperidine in place of 4-(4-fluorobenzoyl)piperidine

EXAMPLES 26 AND 27

The compounds of the following examples are obtained by carrying out the reaction as in Example 1 but using the appropriately substituted piperidines in place of 4-(4-fluorobenzoyl)piperidine.

EXAMPLE 26

3-{2-[4-(3,4-Dichlorobenzoyl)piperidino]ethyl}benzothiazolin-2-one

EXAMPLE 27

3-{2-[4-(4-Trifluoromethylbenzoyl)piperidino]ethyl} benzothiazolin-2-one

EXAMPLES 28 TO 41

The compounds of the following examples are obtained by carrying out the reaction as in Example 4 but replacing 4-(4-fluorobenzoyl)piperidine with the appropriately substituted piperidines:

EXAMPLE 28

3-{2-[4-(4-Methoxybenzoyl)piperidino]ethyl}-6-(4-morpholinobutyl)benzothiazolin-2-one

EXAMPLE 29

3-{2-[4-(4-Trifluoromethylbenzoyl)piperidino]ethyl}-6-(4-morpholinobutyl)benzothiazolin-2-one

EXAMPLE 30

3-{2-[4-(3,4-Dichlorobenzoyl)piperidino]ethyl}-6-(4morpholinobutyl)benzothiazolin-2-one

EXAMPLE 31

3-[2-(4-Benzoylpiperidino)ethyl]-6-(4-morpholinobutyl)benzothiazolin-2-one

EXAMPLE 32

3-{2-[4-(3,5-Dibromo-2,6-dimethoxybenzoyl)piperidino]ethyl}-6-(4-morpholinobutyl)benzothiazolin-2 -one

EXAMPLE 33

3-{2-[4-(4-Chlorobenzoyl)piperidino]ethyl}-6-(4-morpholinobutyl)benzothiazolin-2-one

EXAMPLE 34

3-{2-[4-(3-Phenylpropionyl)piperidino]ethyl}-6-(4-morpholinobutyl)benzothiazolin-2-one

EXAMPLE 35

3-{2-[4-(5-Phenylvaleryl)piperidino]ethyl}-6-(4-morpholinobutyl)benzothiazolin-2-one

EXAMPLE 36

3-{2-{4-[4-(4-Fluorophenyl)butyryl]piperidino}ethyl}-6-(4-morpholinobutyl)benzothiazolin-2-one

EXAMPLE 37

3-{3-[4-(4-Fluorobenzoyl)piperidino]-2-methylpropyl}-6-(4-morpholinobutyl)benzothiazolin-2-one

EXAMPLE 38

3-{2-[4-(6-Fluoronaphthylcarbonyl)piperidino]ethyl}-6-(4-morpholinobutyl)benzothiazolin-2-one

EXAMPLE 39

3-{2-[4-(Naphthylcarbonyl)piperidino]ethyl}-6-(4-morpholinobutyl)benzothiazolin-2-one

EXAMPLE 40

3-{2-[4-(7-Methoxynaphthylcarbonyl)piperidino]ethyl}-6-(4-morpholinobutyl)benzothiazolin-2-one

EXAMPLE 41

3-{4-[4-(4-Fluorobenzoyl)piperidino]butyl}-6-(4-morpholinobutyl)benzothiazolin-2-one

EXAMPLE 42

3-{2-[4-(4-Fluorobenzoyl)piperidino]ethyl}-6-{3-[4-(2-methoxyphenyl)piperazinyl]-2-methylpropyl}benzothiazolin-2-one The title compound is obtained by carrying out the reaction as in Example 1 but replacing benzothiazolin-2-one with 6-{3-[4-(2-methoxyphenyl)piperazinyl]-2-methylpropyl}benzothiazolin-2-one.

EXAMPLE 43

3-{2-[4-(4-Fluorobenzoyl)piperidino]ethyl}benzoxazolin-2-one

The title compound is obtained by carrying out the reaction as in Example 1 but replacing benzothiazolin-2-one with benzoxazolin-2-one.

EXAMPLE 44

3-{2-[4-(4-Fluorobenzoyl)piperidino]ethyl}-6-{4-[4-(3-trifluoromethylphenyl)piperazinyl]butyl}benzoxazolin-2-one The title compound is obtained by carrying out the reaction as in Example 1 but replacing 6-{4-[4-(3-trifluoromethylphenyl)piperazinyl]butyl}benzothiazolin-2-one with 6-{4-[4-(3-trifluoromethylphenyl)piperazinyl]butyl}benzoxazolin-2-one.

EXAMPLE 45

3-{2-[4-(4-Fluorobenzoyl)piperidino]ethyl}-6-{4-[4-(2-methoxyphenyl)piperazinyl]butyl}benzoxazolin-2-one The title compound is obtained by carrying out the reaction as in Example 3 but replacing 6-{4-[4-(2-methoxyphenyl)piperazin-1-yl]butyl}benzothiazolin-2-one with 6-{4-[4-(2-methoxyphenyl)piperazin-1-yl]butyl}benzoxazolin-2-one.

EXAMPLE 46

3-{2-[4-(4-Fluorobenzoyl)piperidino]ethyl}-6-(4-morpholinobutyl)benzoxazolin-2-one The title compound is obtained by carrying out the reaction as in Example 4 but replacing 6-(4-morpholinobutyl)benzothiazolin-2-one with 6-(4-morpholinobutyl)benzoxazolin-2-one.

EXAMPLE 47

3-{2-[4-(4-Fluorobenzoyl)piperazinyl]ethyl}benzothiazolin-2-one

The title compound is obtained by carrying out the reaction as in Example 1 but starting, in Stage A, from piperazine-1-carboxylic acid in place of piperidine-4-carboxylic acid.

EXAMPLE 48

3-Methyl-6-{2-[4-(4-fluorobenzoyl)piperidino]ethyl} benzothiazolin-2-one

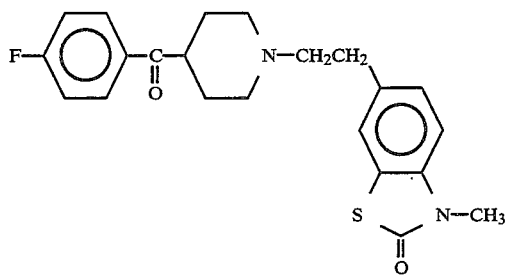

STAGE A

3-Methyl-6-(2-Bromoethyl)benzothiazolin-2-one 0.15 tool of 3-methyl-6-bromoacetylbenzothiazolin-2-one (42.9 g) is dissolved in 1 mol of trifluoroacetic acid (77 cm³) in a 250 cm³ groundneck flask. 0.33 mol of triethylsilane (52.70 cm³) is introduced dropwise using a dropping funnel, with magnetic stirring. A calcium chloride drying tube is fitted and stirring is maintained for the required time at room temperature. The reaction mixture is poured into 500 cm³ of ice-cold water. The precipitate obtained is filtered off, washed with water until the wash liquors are neutral, dried and then recrystallized.

Reaction time: 20 hours
Melting point: 97°–98° C.
Yield: 86%
Recrystallization solvent: cyclohexane
Elemental analysis: Calculated: C % 44.13 H % 3.70 N % 5.15 Found: C % 44.26 H % 3.60 N % 5.34 Infrared spectrometry: 3050–2850 cm$^{-1}$ ν CH (alkyls) 1660 cm$^{-1}$ ν CO (NCOS) 1610–1580 cm$^{-1}$ ν C═C (aromatics)

STAGE B

3-Methyl-6-{2-[4-(4-fluorobenzoyl)piperidino]ethyl}benzothiazolin-2-one 0.01 mol of 3-methyl-6-(2-bromoethyl)benzothiazolin-2-one is dissolved in 50 cm³ of anhydrous acetone. The acetone is heated to reflux. 0.022 mol of triethylamine in solution in 20 cm³ of anhydrous acetone is added and then 0.01 mol of the hydrochloride of 4-(4-fluorobenzoyl)piperidine is added with magnetic stirring. Heating is continued for 24 hours and then the triethylamine hydrobromide formed is filtered off.

The filtrate is evaporated and the residue is taken up in 50 cm³ of a 1M HCl solution. The expected product precipitates, is filtered off, is dried and is then recrystallized.

Melting point (hydrochloride): 224°–226° C.
Yield: 62%
Recrystallization solvent: absolute alcohol
Basic nitrogen assay: for one basic nitrogen Basic nitrogen percentage, theory: 3.22% Basic nitrogen percentage, found: 2.94%

Infrared spectrometry: 3000–2800 cm$^{-1}$ ν CH (alkyls) 2600–2400 cm$^{-1}$ ν NH 1660 cm$^{-1}$ ν CO (NCOS) 1660 cm$^{-1}$ ν CO (ketone) 1600–1580 cm$^{-1}$ ν C═C (aromatics)

EXAMPLE 49

3-Methyl-6-{4-[4-(4-fluorobenzoyl)piperidino]butyl}benzothiazolin-2-one

The title product is obtained by carrying out the reaction as in Example 48 but replacing, in Stage A, 3-methyl-6-bromoacetylbenzothiazolin-2-one with 3-methyl-6-bromobutyrylbenzothiazolin-2-one.

EXAMPLES 50 TO 52

The compounds of the following examples are obtained by carrying out the reaction as in Example 48 but replacing, in Stage B, 4-(4-fluorobenzoyl)piperidine with the appropriately substituted piperidines:

EXAMPLE 50

3-Methyl-6-{4-[4-(4-chlorobenzoyl)piperidino]ethyl}benzothiazolin-2-one

EXAMPLE 51

3-Methyl-6-[4-(4-benzoylpiperidino)ethyl]benzothiazolin-2-one

EXAMPLE 52

3-Methyl-6-{4-[4-(4-methoxybenzoyl)piperidino]ethyl}benzothiazolin-2-one

EXAMPLE 53

3-Methyl-6-{2-[4-(4-methoxybenzoyl)piperidino]ethyl}benzoxazolin-2-one

The title product is obtained by carrying out the reaction as in Example 48 but replacing, in Stage A, 3-methyl-6-bromoacetylbenzothiazolin-2-one with 3-methyl-6-bromoacetylbenzoxazolin-2-one.

EXAMPLE 54

6-{2-[4-(4-Fluorobenzoyl)piperidino]ethyl}benzothiazolin-2-one

The title compound is obtained by carrying out the reaction as in Example 48 but replacing 3-methyl-6-bromoacetylbenzothiazolin-2-one with 6-bromoacetylbenzothiazolin-2-one.

EXAMPLE 55

6-{4-[4-(4-Fluorobenzoyl)piperidino]butyl}benzothiazolin-2-one

The title product is obtained by carrying out the reaction as in Example 48 but replacing, in Stage A, 3-methyl-6-bromoacetylbenzothiazolin-2-one with 6-bromobutyrylbenzothiazolin-2-one.

EXAMPLES 56 TO 58

The compounds of the following examples are obtained by carrying out the reaction as in Example 55 but replacing, in Stage B, 4-(4-fluorobenzoyl)piperidine with the appropriately substituted piperidines:

EXAMPLE 56

6-{4-[4-(4-Chlorobenzoyl)piperidino]butyl}benzothiazolin-2-one

EXAMPLE 57

6-[4-(4-Benzoylpiperidino)butyl]benzothiazolin-2-one

EXAMPLE 58

6-{4-[4-(4-Methoxybenzoyl)piperidino]butyl}benzothiazolin-2-one

EXAMPLE 59

3-Methyl-6-{4-[4-(4-fluorobenzoyl)piperidino]butyl}benzoxazolin-2-one

The title product is obtained by carrying out the reaction as in Example 48 but replacing 3-methyl-6-bromoacetylbenzothiazolin-2-one with 3-methyl-6-bromobutyrylbenzoxazolin-2-one.

EXAMPLES 60 TO 62

The compounds of the following examples are obtained by carrying out the reaction as in Example 59 but replacing, in Stage B, 4-(4-fluorobenzoyl)piperidine with the appropriately substituted piperidines:

EXAMPLE 60

3-Methyl-6-{4-[4-(4-chlorobenzoyl)piperidino]butyl}benzoxazolin-2-one

EXAMPLE 61

3-Methyl-6-[4-(4-benzoylpiperidino)butyl]benzoxazolin-2-one

EXAMPLE 62

3-Methyl-6-{4-[4-(4-methoxybenzoyl)piperidino]butyl}benzoxazolin-2-one

EXAMPLE 63

6-{4-[4-(4-Fluorobenzoyl)piperidino]butyl}benzoxazolin-2-one

The title product is obtained by carrying out the reaction as in Example 48, but replacing 3-methyl-6-bromoacetylbenzothiazolin-2-one with 6-bromobutyrylbenzoxazolin-2-one.

EXAMPLES 64 TO 66

The compounds of the following examples are obtained by carrying out the reaction as in Example 63 but replacing, in Stage B, 4-(4-fluorobenzoyl)piperidine with the appropriately substituted piperidines:

EXAMPLE 64

6-{4-[4-(4-Chlorobenzoyl)piperidino]butyl}benzoxazolin-2-one

EXAMPLE 65

6-[4-(4-Benzoylpiperidino)butyl]benzoxazolin-2-one

EXAMPLE 66

6-{4-[4-(4-Methoxybenzoyl)piperidino]butyl}benzoxazolin-2-one

EXAMPLE A

Measurement of the Affinity for Serotoninergic Receptors

Protocol

The in-vitro affinity of the compounds of the invention was determined:
- for 5-HT$_{1A}$ serotoninergic receptors, by measuring the displacement of 8-OH-DPAT (8-hydroxy-2-(di-n-propylamino)tetralin), on rat hippocampus preparations,
- for 5-HT$_{1C}$ serotoninergic receptors, by measuring the displacement of N-methylmesulergine, on rat frontal cortex and hippocampus preparations,
- for 5-HT$_{1D}$ serotoninergic receptors, by measuring the displacement of 5-hydroxytryptamine, on rat cortex, striatum and globus pallidus preparations,
- for 5-HT$_2$ serotoninergic receptors, by measuring the displacement of aminoiodoketanserin, on rat frontal cortex preparations,
- for 5-HT$_3$ serotoninergic receptors, by measuring the displacement of BRL 43694, on rat area postrema preparations.

Results

The compounds of the invention show a very high affinity for 5-HT$_2$ serotoninergic receptors. As examples, the compounds of Examples 1 and 3 have an IC$_{50}$ (concentration inhibiting binding of the labelled ligand by 50%) of the order of $10^{-9}$M to $10^{-10}$M (compounds of Examples 1 and 3: IC$_{50}$:$10^{-9}$M, compound of Example 4: $5.10^{-10}$M).

The compounds of the invention also show a significant binding selectivity for 5-HT$_2$ receptors with respect to other serotoninergic receptors.

The compounds of Application EP 506539 do not in the least show such an affinity and selectivity for 5-HT$_2$ receptors.

EXAMPLE B

Antipsychotic Activity: Study of Antagonism of Amphetamine-Induced Hyperactivity The selective antagonism of amphetamine-induced hyperactivity is regarded as an indicator of an antipsychotic activity.

Protocol

An injection by the IP route of 2 mg/kg of amphetamine induces a marked measurable hyperactivity. Sprague-Dawley rats weighing 200 to 250 g receive the compounds to be tested by the IP route before administration of the amphetamine and the locomotory activity is then measured 30 minutes later for a period of 30 minutes. 12 animals are tested per dose.

Reference: Costall B. et al.—Brain Res., 123: 89–111.

Results

The compounds of the invention very significantly inhibit amphetamine-induced hyperactivity.

EXAMPLE C

Measurement of Anxiolytic Activity: Light/Dark Cage Test

Rats prefer enclosed and dark spaces to open and illuminated spaces. This preference is reflected in the proportion of time spent in enclosed and dark spaces. A characteristic of anxiolytic compounds is to increase the time spent in open and illuminated spaces.

Protocol

The animals are placed in a cage consisting of 2 compartments, one being open and illuminated and the other being dark and enclosed. The time spent by the animal in each of the compartments, as well as the number of movements from one compartment to the other, is measured for a period of 5 minutes. 10 animals are studied per dose.

Reference: Crawley J. N., Pharmacol. Biochem. Behav., 1981, vol 15, p 695–699.

Results

It clearly appears that the compounds of the invention have an anxiolytic activity since they increase very significantly the time spent by the animals in the illuminated compartment.

EXAMPLE D

Analgesic Activity: Hotplate Test

Rats or mice are placed on a hotplate (58° C.) inside a Plexiglas® cylinder. The reaction time which the animal takes to lick its paws is measured. If no reaction is recorded, the test is terminated after 120 seconds. 10 animals are studied per dose. The tested compound is usually administered i.p. 30 minutes before the test.

16 mg.kg$^{-1}$ i.p. of morphine is used as the reference compound which inhibits the reaction time which the animals takes to lick its paws by 129%.

Reference: Eddy N. B., Liembach D., 1959. Synthetic Analgesics: II-dithienylbutenyl and dithienylbutylamines. J. Pharmacol. Exp. Ther., 107: 385–393.

Results: the compounds of the invention very significantly increase the reaction time which the animal takes to lick its paws. For example, 0.25 mg.kg$^{-1}$ of the compound of Example 48 inhibited this reaction time by 175%.

EXAMPLE E

Measurement of the Toxicity

The toxicity was tested after oral administration of a 650 mg/kg dose to groups of 8 mice (26±2 grams). The animals are observed at regular intervals during the first day and daily during the 2 weeks following the treatment.

It appears that the compounds of the invention are not toxic at a dose of 650 mg/kg, and no disorder is generally observed after administration of such a dose.

EXAMPLE F

Pharmaceutical Composition

Tablet containing a 2.5 mg dose of 3-{2-[4-(4-fluorobenzoyl)piperidino]ethyl}-6-(4-morpholinobutyl)benzothiazolin-2-one

| Preparation for 1000 tablets: | |
| --- | --- |
| 3-{2-[4-(4-Fluorobenzoyl)piperidino]ethyl}-6-(4-morpholinobutyl)benzothiazolin-2-one | 2.5 g |
| Wheat starch | 15 g |
| Maize starch | 15 g |
| Lactose | 65 g |
| Magnesium stearate | 2 g |
| Silica | 1 g |
| Hydroxypropyl cellulose | 2 g |

We claim:

1. A compound which is selected from those of formula (I):

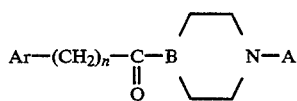

(I)

wherein:
  Ar represents phenyl or naphthyl, Ar being unsubstituted or substituted by one or more radicals selected from halogen, lower alkyl, lower alkoxy, and trifluoromethyl,
  n represents 0 or 1 to 4, inclusive
  B represents

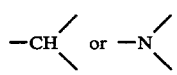

and
A represents a group of formula (A1) or (A2):

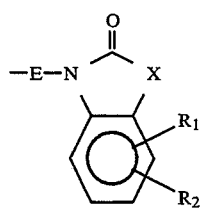

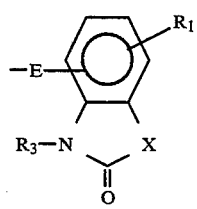

wherein:
  E represents a linear or branched alkylene chain having 1 to 6 carbon atoms, inclusive,
  $R_1$ represents a radical selected from hydrogen, hydroxyl, lower alkyl, and lower alkoxy,
  $R_2$ represents

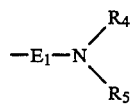

where $E_1$ has the same definition as E as described above and where $R_4$ and $R_5$ are selected, independently from one another, from hydrogen and lower alkyl, or form, together with the nitrogen to which attached, a heterocycle selected from pyrrolidine, piperidine, substituted piperidine, morpholine, piperazine, and substituted piperazine,
  $R_3$ represents a radical selected from hydrogen and lower alkyl, and
  X represents sulfur or oxygen, its optical isomers, in pure form or in the form of a mixture, and addition salts thereof with a pharmaceutically-acceptable base or acid, it being understood that, except when otherwise specified, the terms "lower alkyl" and "lower alkoxy" denote linear or branched groups having 1 to 6 carbon atoms inclusive, and the term "substituted" assumed by the "piperidine" and "piperazine" heterocycles means that these heterocycles can be substituted in the 4-position by a radical selected from lower alkyl, aryl, and lower arylalkyl, the term "aryl" denoting phenyl, naphthyl, or pyridyl, which aryl can itself be unsubstituted or substituted by one or more radicals selected from halogen, lower alkyl, hydroxyl, lower alkoxy, and trifluoromethyl.

2. A compound as claimed in claim 1, wherein Ar represents 4-fluorophenyl, its optical isomers, in pure form or in the form of a mixture, and addition salts thereof with a pharmaceutically-acceptable base or acid.

3. A compound as claimed in claim 1, wherein Ar represents 4-fluorophenyl, n is zero and
  B represents

its optical isomers, in pure form or in the form of a mixture, and addition salts there of with a pharmaceutically-acceptable base or acid.

4. A compound as claimed in claim 1, wherein $R_2$ represents 4-morpholinobutyl, its optical isomers, in pure form or in the form of a mixture, and addition salts thereof with a pharmaceutically-acceptable base or acid.

5. A compound as claimed in claim 1, which is selected from 3-{2-[4-(4-fluorobenzoyl)piperidino]ethyl}-6-{4-[4-(3-trifluoromethylphenyl)piperazinyl]butyl} benzothiazolin-2-one and addition salts thereof with a pharmaceutically-acceptable acid.

6. A compound as claimed in claim 1, which is selected from 3-{2-[4-(4-fluorobenzoyl)piperidino]ethyl}-6-(4-morpholinobutyl)benzothiazolin-2-one and addition salts thereof with a pharmaceutically-acceptable acid.

7. A compound as claimed in claim 1, which is selected from 3-{2-[4-(4-fluorobenzoyl)piperidino]ethyl}-6-{4-[4-(2-methoxyphenyl)piperazinyl]butyl}benzothiazolin-2-one and addition salts thereof with a pharmaceutically-acceptable acid.

8. A pharmaceutical composition containing as active ingredient a compound according to claim 1 in combination with one or more pharmaceutically acceptable excipients or carriers.

9. A method of treating a mammal of pain, comprising the step of administering to the said mammal an amount of a compound according to claim 1 which is effective for treating pain.

* * * * *

UNITED STATES PATENT AND TRADEMARK OFFICE
CERTIFICATE OF CORRECTION

PATENT NO. : 5,387,586
DATED : February 7, 1995
INVENTOR(S) : Ousmane Diouf, Daniel Lesieur, Patrick Depreux, Bèatrice Gaurdiola-Lemaitre Daniel-Henri Caignard, Pierre Renard, Gèrard Adam It is certified that error appears in the above-indentified patent and that said Letters Patent is hereby corrected as shown below:

Column 7, line 13; "25°-256°" should read -- 254°-256° --
Column 10, line 17; "3-{2-[4-(Fluorobenzoyl)" should read
    -- 3-{2-[4-(4-Fluorobenzoyl) --
Column 11, line 13; "(4morpholinobutyl)" should read
    -- (4-morpholinobutyl) --
Column 12, line 66; "tool" should read -- mol --
Column 20, line 15; insert a hyphen "-" between the words
    "pharmaceutically" and "acceptable"

Column 20, line 17; delete the word "of" (2nd occurence) and
    insert the words -- suffering from --

Column 20, line 20; delete the word "treating" and insert the
    words -- alleviation of --

Signed and Sealed this

Thirtieth Day of May, 1995

*Attest:*

BRUCE LEHMAN

*Attesting Officer*  *Commissioner of Patents and Trademarks*